(12) United States Patent
Tai et al.

(10) Patent No.: US 12,170,141 B2
(45) Date of Patent: Dec. 17, 2024

(54) METHOD AND SYSTEM FOR EVALUATING EFFICACY OF A THERAPEUTIC INTERVENTION

(71) Applicant: Histoindex Pte Ltd, Singapore (SG)

(72) Inventors: Chi Shang Tai, Singapore (SG); Yayun Ren, Singapore (SG)

(73) Assignee: Histoindex Pte Ltd., Singapore (SG)

( * ) Notice: Subject to any disclaimer, the term of this patent is extended or adjusted under 35 U.S.C. 154(b) by 299 days.

(21) Appl. No.: 17/789,657

(22) PCT Filed: Jan. 7, 2021

(86) PCT No.: PCT/SG2021/050007
§ 371 (c)(1),
(2) Date: Jun. 28, 2022

(87) PCT Pub. No.: WO2021/141537
PCT Pub. Date: Jul. 15, 2021

(65) Prior Publication Data
US 2023/0033034 A1  Feb. 2, 2023

Related U.S. Application Data

(60) Provisional application No. 62/958,520, filed on Jan. 8, 2020.

(51) Int. Cl.
*G16H 30/40* (2018.01)
*G01N 21/64* (2006.01)
(Continued)

(52) U.S. Cl.
CPC ......... *G16H 30/40* (2018.01); *G01N 21/6458* (2013.01); *G06T 7/0016* (2013.01);
(Continued)

(58) Field of Classification Search
CPC .... G16H 30/40; G16H 50/30; G01N 21/6458; G06T 7/0016
See application file for complete search history.

(56) References Cited

U.S. PATENT DOCUMENTS

2010/0278405 A1* 11/2010 Kakadiaris ............. G16H 50/30
382/131
2017/0329894 A1* 11/2017 Kennedy ................ G16H 40/63

* cited by examiner

*Primary Examiner* — David Bilodeau
(74) *Attorney, Agent, or Firm* — Dickinson Wright PLLC

(57) ABSTRACT

A method for evaluating efficacy of a therapeutic intervention includes obtaining, from each of paired liver biopsy samples of a subject comprising a first sample prior to the therapeutic intervention and a second sample after the therapeutic intervention, a first set of image data indicative of a first histopathological feature and a second set of image data indicative of a second histopathological feature. For each of the first and second samples, the second histopathological feature is quantified, the first and second sets of image data are overlapped based on a common reference frame, and the first histopathological feature present in an overlapping area of the first and second sets of image data is quantified. The method also includes determining the efficacy of the therapeutic intervention based on a comparison of the quantified second histopathological feature between the first and second samples and/or a comparison of the quantified first histopathological feature in the overlapping area between the first and second samples. The first and second pathological features include features selected from the group consisting of fibrosis, inflammation, ballooning and steatosis.

14 Claims, 7 Drawing Sheets

(51) Int. Cl.
*G06T 7/00* (2017.01)
*G16H 50/30* (2018.01)

(52) U.S. Cl.
CPC ... *G16H 50/30* (2018.01); *G06T 2207/10056* (2013.01); *G06T 2207/30024* (2013.01); *G06T 2207/30056* (2013.01)

METHOD AND SYSTEM FOR EVALUATING EFFICACY OF A THERAPEUTIC INTERVENTION

This application is a U.S. National Stage application of PCT International Application No. PCT/SG2021/050007, filed Jan. 7, 2021, which claims priority from U.S. Provisional Application No. 62/958,520, filed Jan. 8, 2020.

FIELD OF INVENTION

The present invention relates broadly, but not exclusively, to methods and systems for evaluating efficacy of a therapeutic intervention, such as a therapy for a liver disease.

BACKGROUND

Nonalcoholic fatty liver disease (NAFLD), such as Nonalcoholic steatohepatitis (NASH), is a common cause of chronic liver disease worldwide. Various therapeutics are being developed for NASH and clinical trials are conducted to assess efficacy of such therapeutics. Although non-invasive biomarkers, including imaging techniques, are promising tools to assess disease severity in NAFLD, none have been validated or qualified as trial endpoints, and none can accurately assess grade of steatosis, ballooning of hepatocytes, or liver inflammation. Therefore, histological assessment remains the reference standard for diagnosing NASH.

Clinical trials normally use the NASH Clinical Research Network (CRN) system for semi-quantitative histological assessment of disease severity. Inter-observer variability may hamper histological assessment, and diagnostic consensus is not always achieved. In addition, current scoring systems only provide a nonlinear, semi-quantitative, or categorical assessment of disease. This may limit precision and granularity of data, particularly in the context of subtle changes with therapy.

A need therefore exists to provide a method and system that can address at least one of the above problems.

SUMMARY

An aspect of the present disclosure provides a method for evaluating efficacy of a therapeutic intervention. The method comprises obtaining, from each of paired liver biopsy samples of a subject comprising a first sample prior to the therapeutic intervention and a second sample after the therapeutic intervention, a first set of image data indicative of a first histopathological feature and a second set of image data indicative of a second histopathological feature; for each of the first and second samples, quantifying the second histopathological feature, overlapping the first and second sets of image data based on a common reference frame, and quantifying the first histopathological feature present in an overlapping area of the first and second sets of image data; and determining the efficacy of the therapeutic intervention based on a comparison of the quantified second histopathological feature between the first and second samples and/or a comparison of the quantified first histopathological feature in the overlapping area between the first and second samples. The first and second pathological features comprise features selected from the group consisting of fibrosis, inflammation, ballooning and steatosis.

Another aspect of the present disclosure provides a system for evaluating efficacy of a therapeutic intervention. The system comprises a data receiving module configured to receive image data generated by each of paired liver biopsy samples of a subject comprising a first sample prior to the therapeutic intervention and a second sample after the therapeutic intervention, wherein the image data comprises a first set of image data indicative of a first histopathological feature and a second set of image data indicative of a second histopathological feature; at least one processor; and a computer-readable memory coupled to the processor and having instructions stored thereon that are executable by the processor to, for each of the first and second samples, quantify the second histopathological feature, overlap the first and second sets of image data based on a common reference frame, and quantify the first histopathological feature present in an overlapping area of the first and second sets of image data; and determine the efficacy of the therapeutic intervention based on a comparison of the quantified second histopathological feature between the first and second samples and/or a comparison of the quantified first histopathological feature in the overlapping area between the first and second samples. The first and second pathological features comprise features selected from the group consisting of fibrosis, inflammation, ballooning and steatosis.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
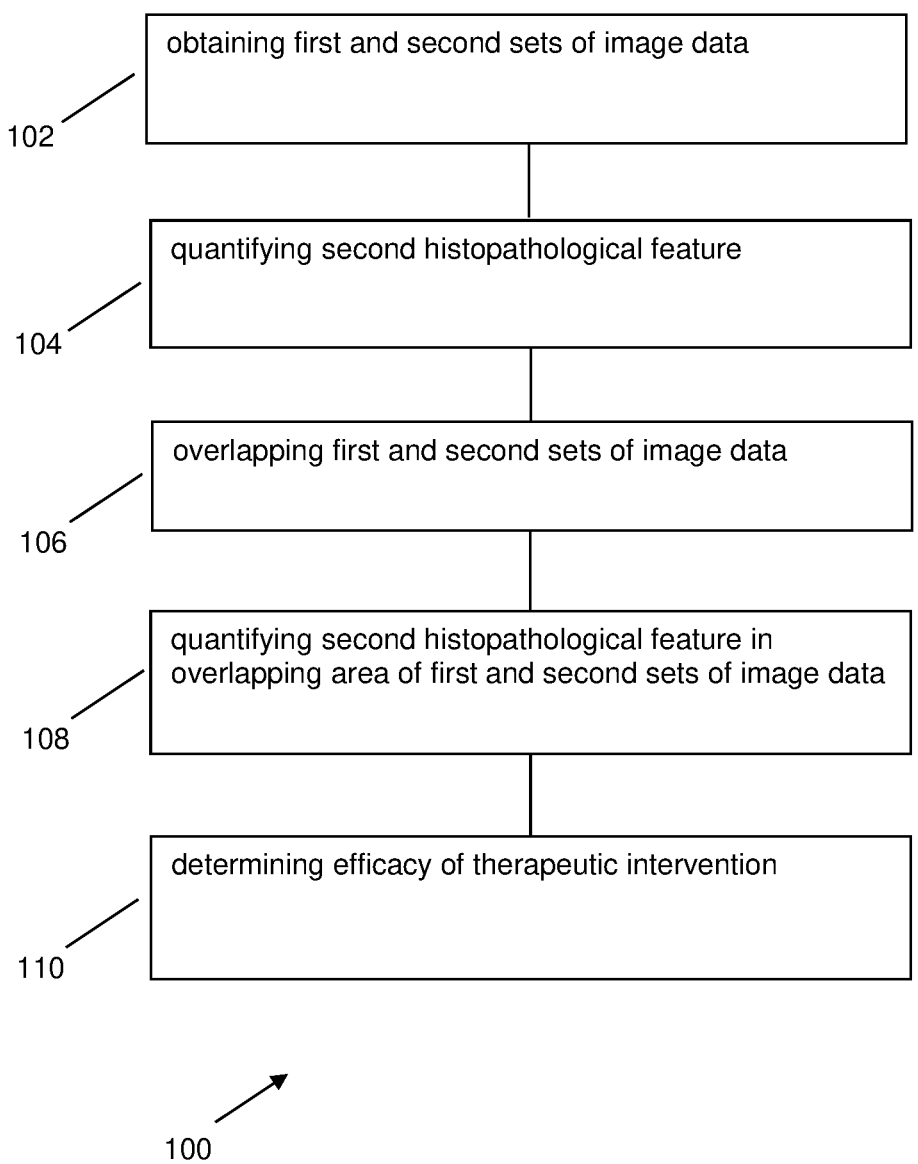
FIG. 1 shows a flow chart illustrating a method for evaluating efficacy of a therapeutic intervention according to an example embodiment.

FIG. 1 shows a flow chart 100 illustrating a method for evaluating efficacy of a therapeutic intervention. At step 102, a first set of image data indicative of a first histopathological feature and a second set of image data indicative of a second histopathological feature are obtained from each of paired liver biopsy samples of a subject. The first and second pathological features include features selected from the group consisting of fibrosis, inflammation, ballooning and steatosis. The paired liver biopsy samples include a first sample taken prior to the therapeutic intervention and a second sample taken after the therapeutic intervention. For each of the first and second samples, the second histopathological feature is quantified (step 104), the first and second sets of image data are overlapped based on a common reference frame (step 106), and the first histopathological feature present in an overlapping area of the first and second sets of image data is quantified (step 108). At step 110, the efficacy of the therapeutic intervention is determined based on a comparison of the quantified second histopathological feature between the first and second samples and/or a comparison of the quantified first histopathological feature in the overlapping area between the first and second samples.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "quantifying", "overlapping", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a computer or other device selectively activated or reconfigured by a computer program stored in the computer. The algorithms and displays presented herein are not inherently related to any particular computer or other apparatus. Various machines may be used with programs in accordance with the teachings herein. Alternatively, the construction of more specialized apparatus to perform the required method steps may be appropriate. The structure of a conventional computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a computer. The computer readable medium may also include a hard-wired medium such as exemplified in the Internet system, or wireless medium such as exemplified in the GSM, GPRS, 3G or 4G mobile telephone systems, as well as other wireless systems such as Bluetooth, ZigBee, Wi-Fi. The computer program when loaded and executed on such a computer effectively results in an apparatus that implements the steps of the preferred method.

The present invention may also be implemented as hardware modules. More particularly, in the hardware sense, a module is a functional hardware unit designed for use with other components or modules. For example, a module may be implemented using discrete electronic components, or it can form a portion of an entire electronic circuit such as an Application Specific Integrated Circuit (ASIC) or Field Programmable Gate Array (FPGA). Numerous other possibilities exist. Those skilled in the art will appreciate that the system can also be implemented as a combination of hardware and software modules.

Example

Drug A is a second-generation insulin sensitizer designed to selectively modulate the mitochondrial pyruvate carrier (MPC), which at the cellular level mediates the effects of over-nutrition, a major cause of NASH and other metabolic disorders. The 12-month analysis conducted in 100 patients demonstrated that drug A treated patients had significant and durable dose-dependent improvements in liver enzymes, glycemic control and improvement in biomarkers of liver injury. Standard single read biopsy demonstrated a dose dependent reduction in NAFLD activity score (NAS) score and steatosis, with a trend for a dose-dependent improvement in NASH resolution and fibrosis improvement. Re-reads of the qualifying biopsy, however, revealed poor intra-reader agreement and imprecision of NASH CRN biopsy reads. Using the 100 patients in a retrospective study, the association between steatosis reduction and fibrosis reduction when measured as a continuous variable using second harmonic generation (SHG)/two-photon excited fluorescence (TPEF) microscopy imaging of paired liver biopsy samples was assessed using the method as described above.

Method:

100 paired liver biopsies from sites with unstained slides available in the study were examined. Qualifying biopsy confirmed NASH (NAS≥4, F1-F3, with at least 50% F2/F3). Fibrosis and steatosis changes were measured in a subset of paired liver biopsies using SHG/TPEF by readers blinded to treatment code. A quantitative steatosis score (qSteatosis) was obtained for the overall sample; and in periportal region (Zone 1), pericentral region (Zone 3), and transitional region in between (Zone 2). Fibrosis changes (e.g. changes in collagen fibers) around the fat vacuoles were measured concomitantly.

Figure 2A:
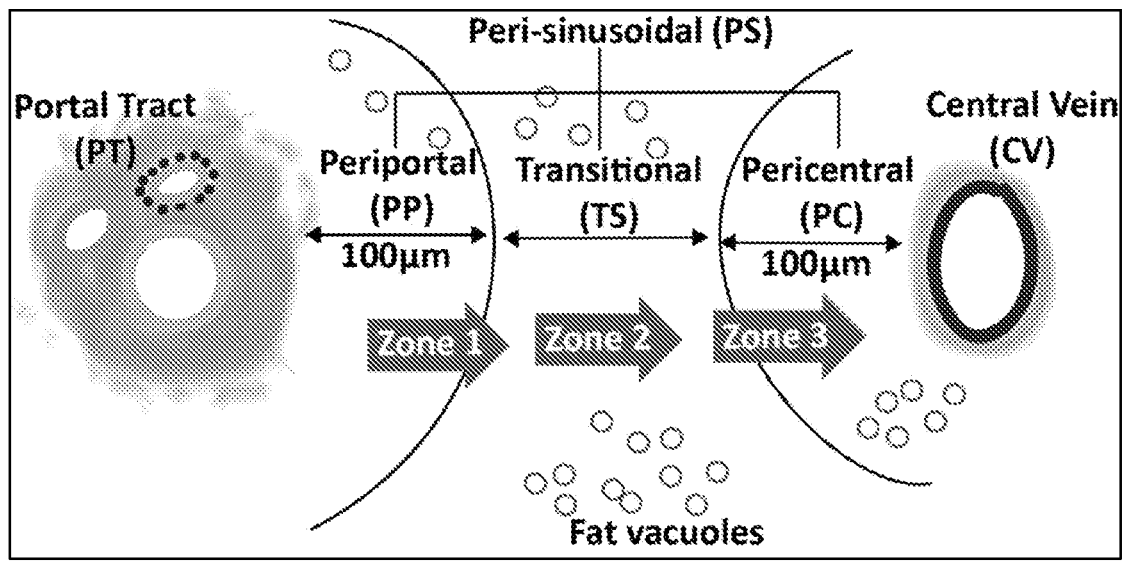
FIG. 2a show a schematic diagram of various regions in a biopsy sample according to an example embodiment.
Figure 2B:
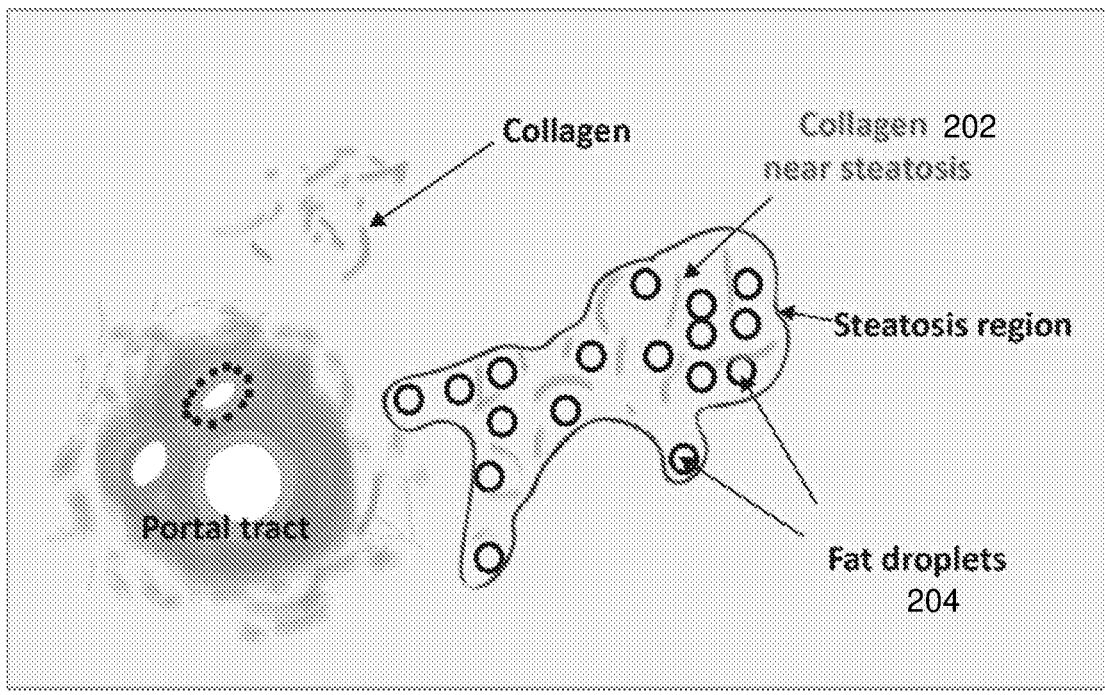
FIG. 2b shows a schematic diagram of a quantification of fibrosis around steatosis according to an example embodiment.

FIG. 2a shows a schematic diagram illustrating an example distribution of Zones 1-3. FIG. 2b shows a quantification of collagen 202 near steatosis (represented by fat droplets 204) by overlapping image analysis of SHG/TPE scanned images.

Results

In patients with reduced qSteatosis score, drug A treated patients (n=50) showed significant decrease in qSteatosis across all three zones; as compared to the placebo (n=50), which only showed significant qSteatosis reduction in Zone 2. Concomitant zonal analysis of fibrosis around the steatosis revealed that there was no significant reduction in fibrosis in all three zones for the placebo-treatment patients, but drug A treated patients clearly indicated a significant reduction in fibrosis in Zone 2. There was a clear difference in the pattern of co-localization in treated versus placebo cohorts.

Figure 3:
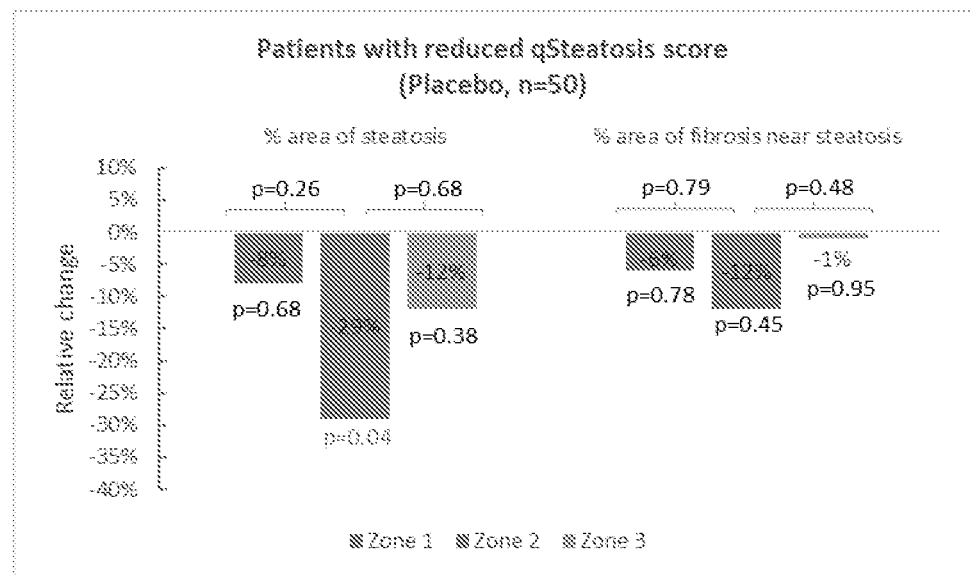
FIG. 3 shows diagrams of relative changes in steatosis and fibrosis near steatosis in various regions/zones for patients receiving placebo treatment.
Figure 4:
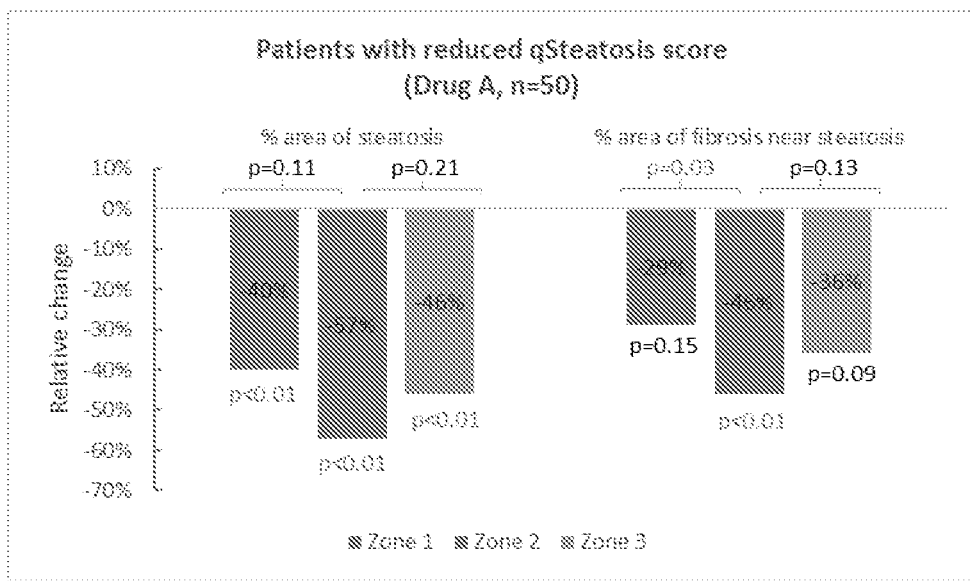
FIG. 4 shows diagrams of relative changes in steatosis and fibrosis near steatosis in various regions/zones for patients receiving drug A treatment.

FIG. 3 shows diagrams of relative changes in steatosis and fibrosis near steatosis in various regions/zones for patients receiving placebo treatment. FIG. 4 shows diagrams of relative changes in steatosis and fibrosis near steatosis in various regions/zones for patients receiving drug A treatment. It can be seen from FIG. 3 that, based on a concomitant zonal analysis of fibrosis around the steatosis, no significant reduction in fibrosis was observed in all three zones for the placebo-treated patients. In contrast, drug A treated patients clearly indicated a significant reduction in fibrosis in Zone 2. For example, FIG. 4 shows that a relative decrease of 57% in qSteatosis in Zone 2 was associated with a relative decrease of 46% in a quantified fibrosis score (qFibrosis) in Zone 2.

Figure 5A:
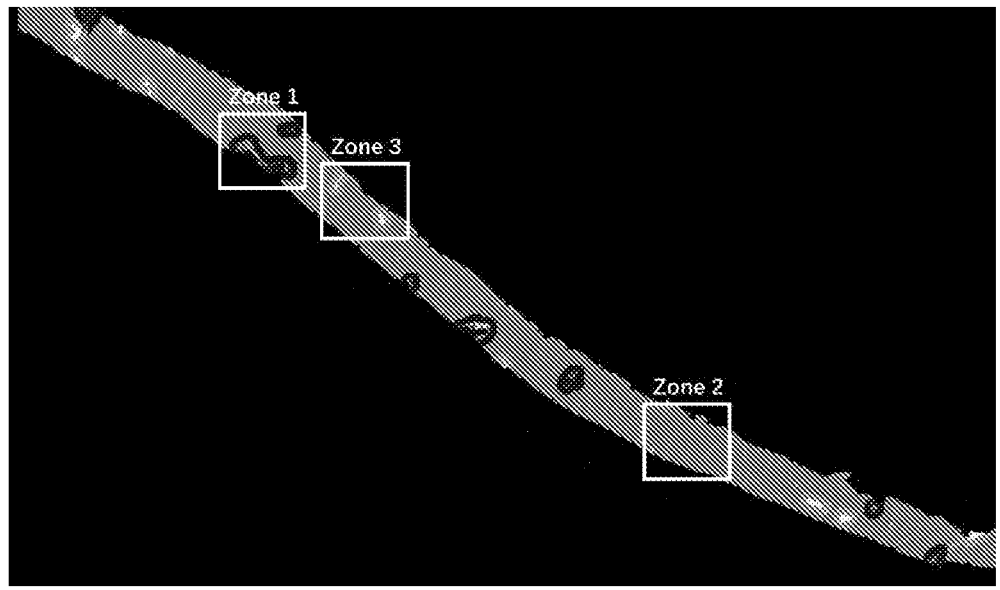
FIG. 5a shows example zones/regions in a biopsy sample taken before treatment.
Figure 5B:
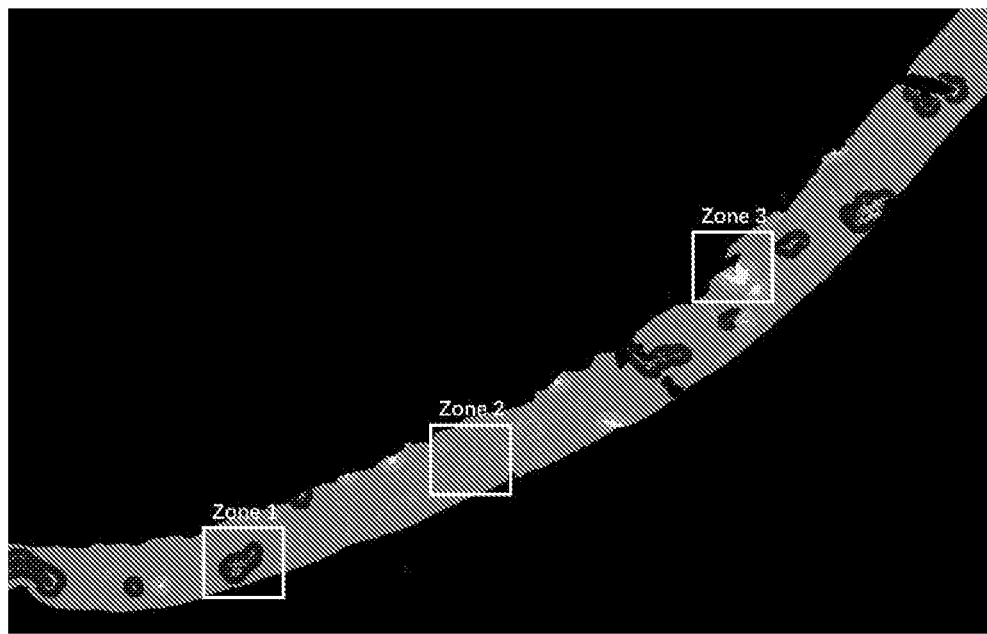
FIG. 5b shows example zones/regions in a biopsy sample taken after treatment.
Figure 5C:
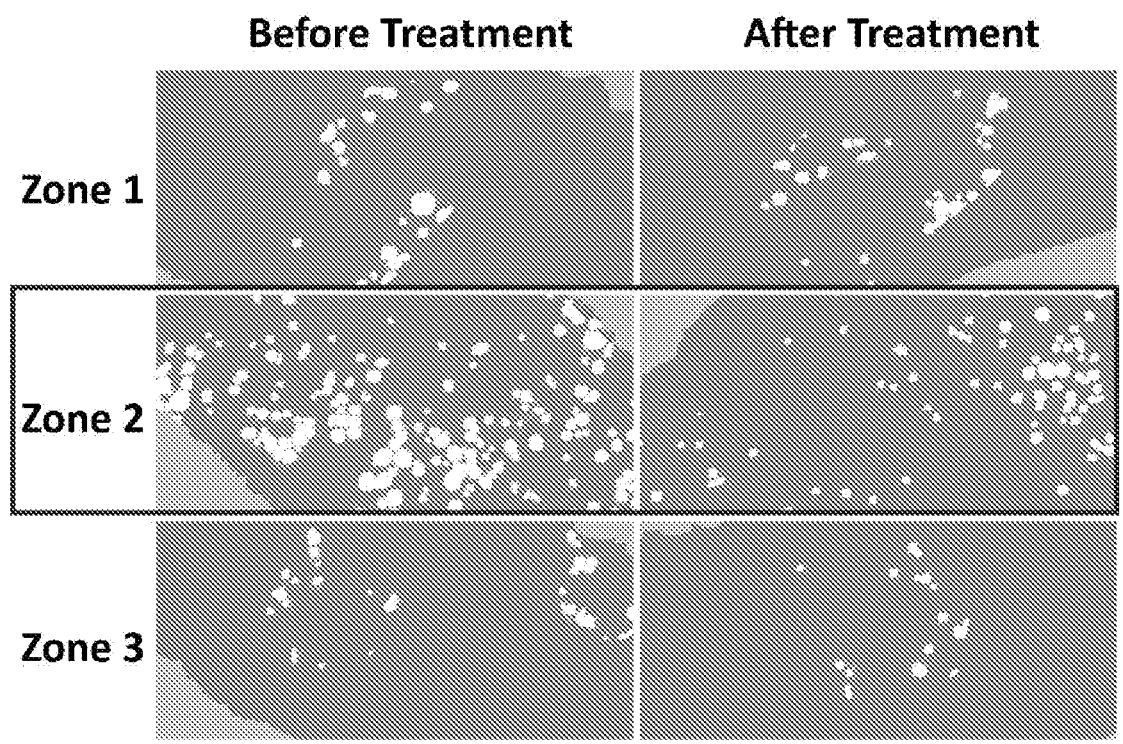
FIG. 5c shows enlarged images of the zones/regions in FIGS. 5a and 5b side by side.

FIGS. 5a-5c show an illustration of how co-localization can reveal steatosis and concomitant fibrosis changes in specific regions of the liver biopsy. The image in FIG. 5a is taken from a liver biopsy sample before treatment, and includes examples of Zones 1-3. The image in FIG. 5b is taken from a liver biopsy sample after treatment, and similarly includes examples of Zones 1-3. FIG. 5c shows enlarged images of Zones 1-3 of both samples when compared side by side. In each image in FIG. 5c, fibrosis and steatosis data are co-localised (e.g. overlapped/superimposed on the same image frame). It can be seen from FIG. 5c that the observational results are consistent with the quantitative results discussed above (e.g. substantial reduction in fibrosis around steatosis in Zone 2 after treatment).

Figure 6:
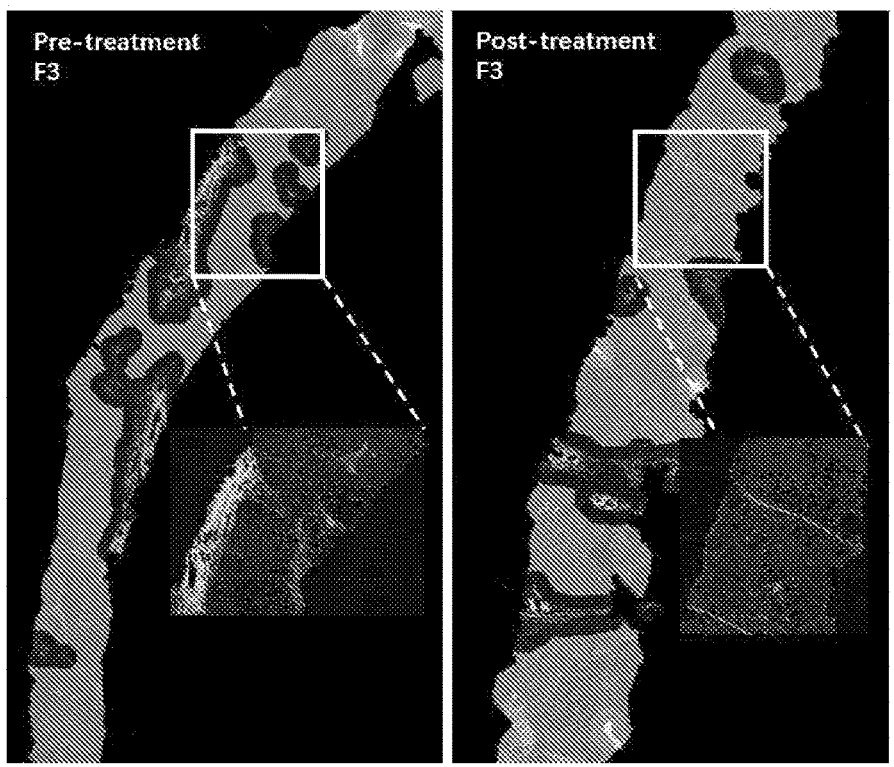
FIG. 6 shows example images for assessing bridging fibrosis regression in Zone 2.
Figure 7:
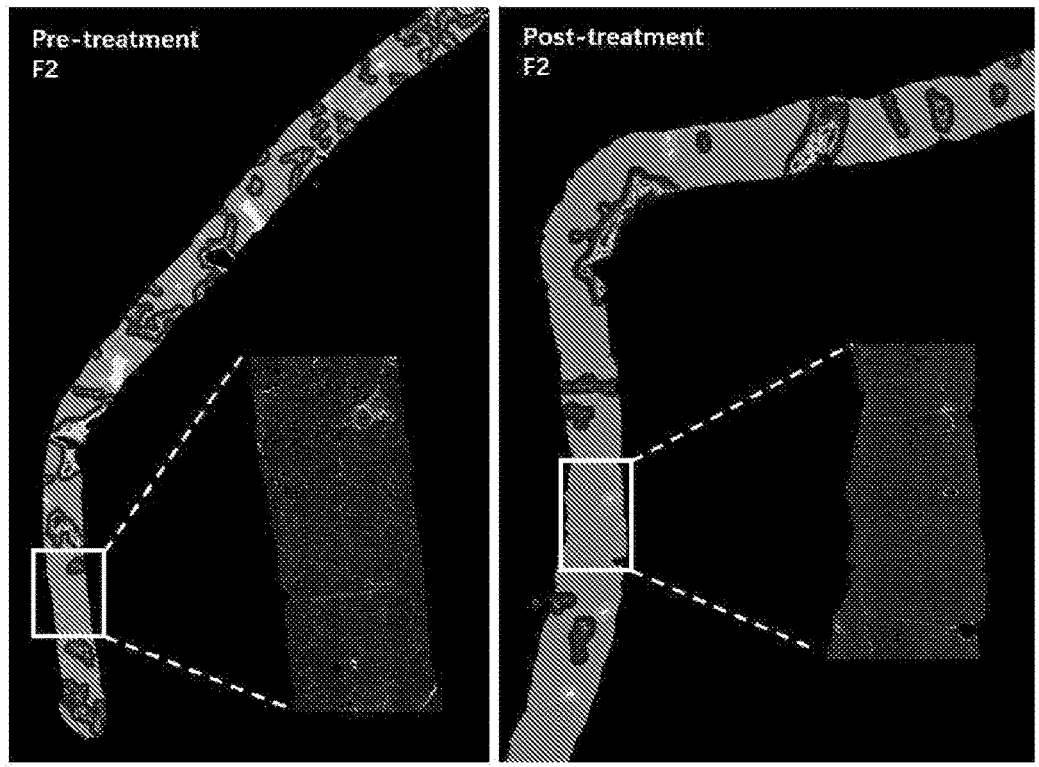
FIG. 7 shows example images for assessing "peri" fibrosis regression.

FIGS. 6 and 7 show images illustrating additional observational results confirming the efficacy of the treatment. In FIG. 6, bridging fibrosis regression in Zone 2 was assessed based on pre-treatment and post-treatment biopsy samples with F3 score. In FIG. 7, peri fibrosis regression was assessed based on pre-treatment and post-treatment biopsy samples with F2 score. It can be seen in FIGS. 6 and 7 from a comparison of each set of samples, that there was a reduction in the number of fibrosis around steatosis and a reduction in peri-portal and peri-venular fibrosis. FIG. 6 additionally reveals a thinning of bridges and a reduction in number of bridges, while FIG. 7 additionally reveals a thinning of collagen fibres and a reduction in number of fibre intersections.

It is noted from this example that drug A treated patients demonstrated a greater reduction in qSteatosis and qFibrosis across all zones as compared to placebo-treated patients. The use of a continuous variable in liver biopsy assessment provides quantitation of zonal changes in steatosis and fibrosis, which cannot be captured using the NASH CRN system. For example, the changes can be expressed in percentage reduction which may be more useful than discrete scores on a whole-number scale such as one used in the NASH CRN system. Further, concomitant qSteatosis and qFibrosis analyses on the same biopsy can reveal mechanism of action (MOA) and is vital for the assessment of therapeutic efficacy.

Figure 8:
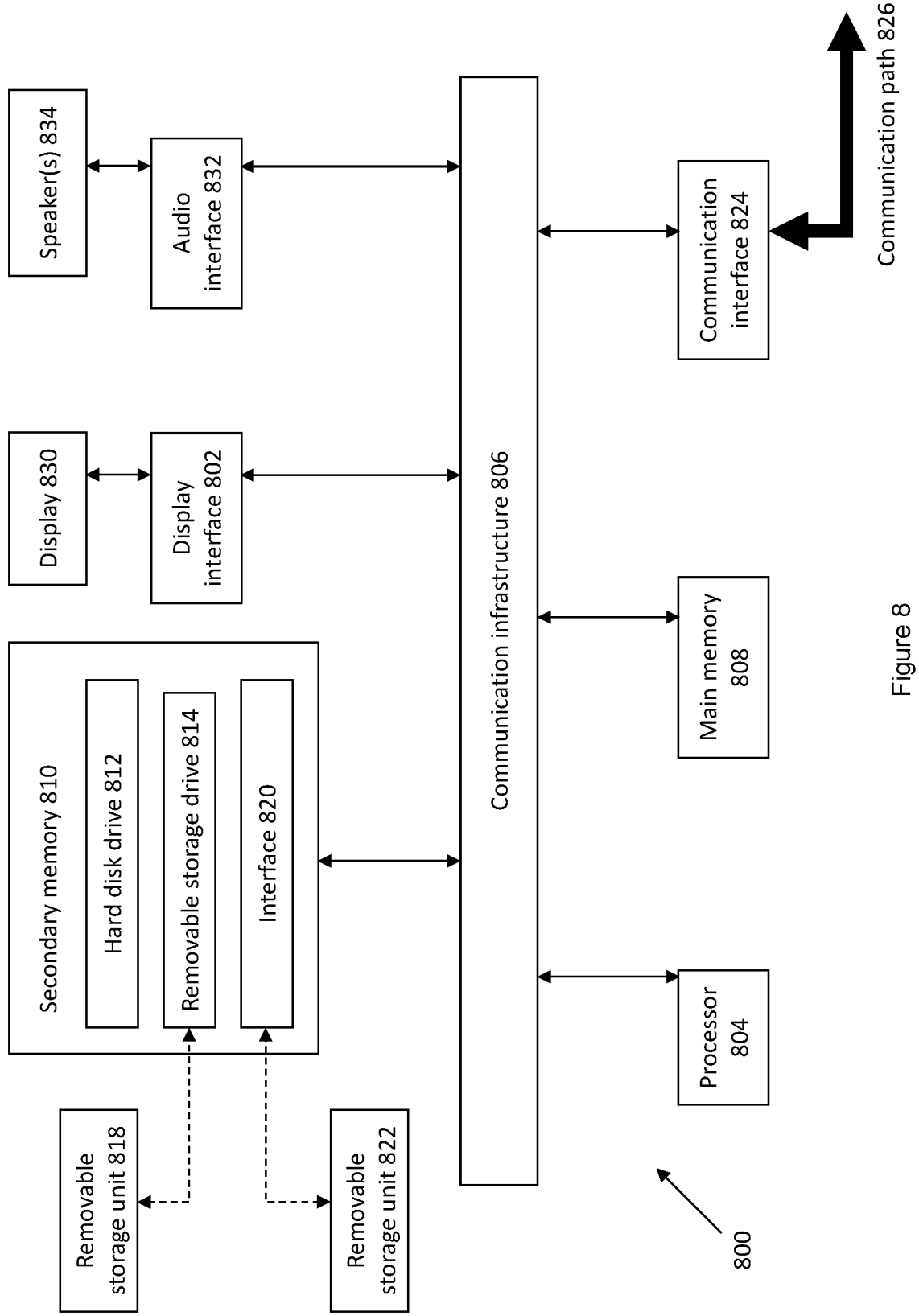
FIG. 8 shows a schematic diagram of a computer device capable of implementing aspects of the present method and system.

FIG. 8 depicts an exemplary computing device 800, hereinafter interchangeably referred to as a computer system 800, where one or more such computing devices 800 may be used for at least some steps of the present method. For example, a system that performs the present method of evaluating efficacy of a therapeutic intervention may include the computing device 800 connected to an image data acquisition device, such as a second harmonic generation (SHG) microscope and/or a two photon excitation fluorescence (TPEF) microscope (not shown). Alternatively, the system may include a stand-alone computing device 800 and receive image data that has been acquired separately. The following description of the computing device 800 is provided by way of example only and is not intended to be limiting.

As shown in FIG. 8, the example computing device 800 includes a processor 804 for executing software routines. Although a single processor is shown for the sake of clarity, the computing device 800 may also include a multi-processor system. The processor 804 is connected to a communication infrastructure 806 for communication with other components of the computing device 800. The communication infrastructure 806 may include, for example, a communications bus, cross-bar, or network.

The computing device 800 further includes a main memory 808, such as a random access memory (RAM), and a secondary memory 810. The secondary memory 810 may include, for example, a hard disk drive 812 and/or a removable storage drive 814, which may include a floppy disk drive, a magnetic tape drive, an optical disk drive, or the like. The removable storage drive 814 reads from and/or writes to a removable storage unit 818 in a well-known manner. The removable storage unit 818 may include a floppy disk, magnetic tape, optical disk, or the like, which is read by and written to by removable storage drive 814. As will be appreciated by persons skilled in the relevant art(s), the removable storage unit 818 includes a computer readable storage medium having stored therein computer executable program code instructions and/or data.

In an alternative implementation, the secondary memory 810 may additionally or alternatively include other similar means for allowing computer programs or other instructions to be loaded into the computing device 800. Such means can include, for example, a removable storage unit 822 and an interface 820. Examples of a removable storage unit 822 and interface 820 include a program cartridge and cartridge interface (such as that found in video game console devices), a removable memory chip (such as an EPROM or PROM) and associated socket, and other removable storage units 822 and interfaces 820 which allow software and data to be transferred from the removable storage unit 822 to the computer system 800.

The computing device 800 also includes at least one communication interface 824. The communication interface 824 allows software and data to be transferred between computing device 800 and external devices via a communication path 826. In various embodiments of the inventions, the communication interface 824 permits data to be transferred between the computing device 800 and a data communication network, such as a public data or private data communication network. The communication interface 824 may be used to exchange data between different computing devices 800 which such computing devices 800 form part an interconnected computer network. Examples of a communication interface 824 can include a modem, a network interface (such as an Ethernet card), a communication port, an antenna with associated circuitry and the like. The communication interface 824 may be wired or may be wireless. Software and data transferred via the communication interface 824 are in the form of signals which can be electronic, electromagnetic, optical or other signals capable of being received by communication interface 824. These signals are provided to the communication interface via the communication path 826.

As shown in FIG. 8, the computing device 800 further includes a display interface 802 which performs operations for rendering images to an associated display 830 and an audio interface 832 for performing operations for playing audio content via associated speaker(s) 834.

As used herein, the term "computer program product" may refer, in part, to removable storage unit 818, removable storage unit 822, a hard disk installed in hard disk drive 812, or a carrier wave carrying software over communication path 826 (wireless link or cable) to communication interface 824. Computer readable storage media refers to any non-transitory tangible storage medium that provides recorded instructions and/or data to the computing device 800 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computing device 800. Examples of transitory or non-tangible computer readable transmission media that may also participate in the provision of software, application programs, instructions and/or data to the computing device 800 include radio or infra-red transmission channels as well as a network connection to another computer or networked device, and the Internet or Intranets including e-mail transmissions and information recorded on Websites and the like.

The computer programs (also called computer program code) are stored in main memory 808 and/or secondary memory 810. Computer programs can also be received via the communication interface 824. Such computer programs, when executed, enable the computing device 800 to perform one or more features of embodiments discussed herein. In various embodiments, the computer programs, when executed, enable the processor 804 to perform features of the above-described embodiments. Accordingly, such computer programs represent controllers of the computer system 800.

Software may be stored in a computer program product and loaded into the computing device 800 using the removable storage drive 814, the hard disk drive 812, or the interface 820. Alternatively, the computer program product may be downloaded to the computer system 800 over the communications path 826. The software, when executed by the processor 804, causes the computing device 800 to perform functions of embodiments described herein.

It is to be understood that the embodiment of FIG. 8 is presented merely by way of example. Therefore, in some embodiments one or more features of the computing device 800 may be omitted. Also, in some embodiments, one or more features of the computing device 800 may be combined together. Additionally, in some embodiments, one or more features of the computing device 800 may be split into one or more component parts.

It will be appreciated that the elements illustrated in FIG. 8 function to provide means for performing the various functions and operations of the servers as described in the above embodiments.

In an implementation, a server may be generally described as a physical device comprising at least one processor and at least one memory including computer program code. The at least one memory and the computer program code are configured to, with the at least one processor, cause the physical device to perform the requisite operations.

It will be appreciated by a person skilled in the art that numerous variations and/or modifications may be made to the present invention as shown in the specific embodiments without departing from the scope of the invention as broadly described. The present embodiments are, therefore, to be considered in all respects to be illustrative and not restrictive.

The invention claimed is:

1. A method for evaluating efficacy of a therapeutic intervention, the method comprising:
obtaining, from each of paired liver biopsy samples of a subject comprising a first sample prior to the therapeutic intervention and a second sample after the therapeutic intervention, a first set of image data indicative of a first histopathological feature and a second set of image data indicative of a second histopathological feature;
for each of the first and second samples:
quantifying the second histopathological feature;
overlapping the first and second sets of image data based on a common reference frame; and
quantifying the first histopathological feature present in an overlapping area of the first and second sets of image data; and
determining the efficacy of the therapeutic intervention based on a comparison of the quantified second histopathological feature between the first and second samples and/or a comparison of the quantified first histopathological feature in the overlapping area between the first and second samples,
wherein the first and second pathological features comprise features selected from the group consisting of fibrosis, inflammation, ballooning and steatosis.

2. The method as claimed in claim 1, wherein the first histopathological feature comprises fibrosis and the second histopathological feature comprises steatosis, and wherein quantifying the first histopathological feature present in the overlapping area comprises a concomitant zonal analysis of changes in collagen fibers around fat vacuoles.

3. The method as claimed in claim 2, further comprising identifying in each of the first and second samples a periportal region, a pericentral region, and a transitional region between the periportal and pericentral regions, wherein quantifying the second histopathological feature comprises quantifying steatosis in the whole sample and each of the periportal, pericentral and transitional regions.

4. The method as claimed in claim 3, wherein the therapeutic intervention is determined to be effective if the quantified steatosis in each of the periportal, pericentral and transitional regions is lower in the second sample than in the first sample.

5. The method as claimed in claim 3, wherein the overlapping area corresponds to the transitional region, and wherein the therapeutic intervention is determined to be effective if the quantified fibrosis in the transitional region is lower in the second sample than in the first sample.

6. The method as claimed in claim 1, wherein obtaining the first and second sets of image data comprises using second harmonic generation (SHG) microscopy and/or two photon excitation fluorescence (TPEF) microscopy.

7. The method as claimed in claim 1, wherein the first histopathological feature comprises fibrosis and the second histopathological feature comprises ballooning.

8. A system for evaluating efficacy of a therapeutic intervention, the system comprising:
a data receiving module configured to receive image data generated by each of paired liver biopsy samples of a subject comprising a first sample prior to the therapeutic intervention and a second sample after the therapeutic intervention, wherein the image data comprises a first set of image data indicative of a first histopathological feature and a second set of image data indicative of a second histopathological feature;

at least one processor; and a computer-readable memory coupled to the processor and having instructions stored thereon that are executable by the processor to:

for each of the first and second samples:
quantify the second histopathological feature;
overlap the first and second sets of image data based on a common reference frame; and
quantify the first histopathological feature present in an overlapping area of the first and second sets of image data; and determine the efficacy of the therapeutic intervention based on a comparison of the quantified second histopathological feature between the first and second samples and/or a comparison of the quantified first histopathological feature in the overlapping area between the first and second samples, wherein the first and second pathological features comprise features selected from the group consisting of fibrosis, inflammation, ballooning and steatosis.

9. The system as claimed in claim 8, wherein the first histopathological feature comprises fibrosis and the second histopathological feature comprises steatosis, and wherein the instructions are executable by the processor to quantify the first histopathological feature present in the overlapping area based on a concomitant zonal analysis of changes in collagen fibers around fat vacuoles.

10. The system as claimed in claim 9, the instructions are executable by the processor to identify in each of the first and second samples a periportal region, a pericentral region, and a transitional region between the periportal and pericentral regions, and to quantify the second histopathological feature based on a quantified steatosis in the whole sample and each of the periportal, pericentral and transitional regions.

11. The system as claimed in claim 10, wherein the therapeutic intervention is determined to be effective if the quantified steatosis in each of the periportal, pericentral and transitional regions is lower in the second sample than in the first sample.

12. The system as claimed in claim 10, wherein the overlapping area corresponds to the transitional region, and wherein the therapeutic intervention is determined to be effective if the quantified fibrosis in the transitional region is lower in the second sample than in the first sample.

13. The system as claimed in claim 8, wherein the image data comprises data from a second harmonic generation (SHG) microscope and/or a two photon excitation fluorescence (TPEF) microscope.

14. The system as claimed in claim 8, wherein the first histopathological feature comprises fibrosis and the second histopathological feature comprises ballooning.

* * * * *